United States Patent [19]

Yoneda

[11] Patent Number: 4,567,260
[45] Date of Patent: Jan. 28, 1986

[54] SYNTHESIS OF 5-DEAZARIBOFLAVINE

[75] Inventor: Fumio Yoneda, Kumamoto, Japan

[73] Assignee: Toyo Jozo Kabushiki Kaisha, Shizuoka, Japan

[21] Appl. No.: 509,764

[22] Filed: Jun. 30, 1983

[30] Foreign Application Priority Data

Jul. 1, 1982 [JP] Japan .................................. 57-115175

[51] Int. Cl.[4] .................... C07D 471/04; C07D 239/54
[52] U.S. Cl. ....................................... 544/250; 544/313
[58] Field of Search ........................ 544/250, 313, 314

[56] References Cited

U.S. PATENT DOCUMENTS 4,079,069  3/1978  Graham et al. ...................... 544/250
4,277,603  7/1981  Tolman et al. ...................... 544/250
4,299,961  11/1981 De Pasquale et al. ......... 544/313 X

FOREIGN PATENT DOCUMENTS 0579573  8/1977  U.S.S.R. .

OTHER PUBLICATIONS

Kazimierczuk et al., Chemical Abstracts, vol. 78, 58339u, (1973).
Yoneda et al., J. Chem. Soc., Perkin Trans. 1, 1976, (16), pp. 1805–1808, (1976).
Kochkanyan et al., Chemical Abstracts, vol. 88, 74409d and Chemical Subject Index, 10 Collective Index, p. 46526CS, (1978).
Yoneda et al., Methods Enzymol. 1980, 66 (Vitam. Coenzymes, Pt. E), pp. 267–277, (1980).

*Primary Examiner*—Donald G. Daus
*Assistant Examiner*—Diana G. Rivers
*Attorney, Agent, or Firm*—Holman & Stern

[57] ABSTRACT

A new synthesis of 5-deazariboflavine is afforded by condensing N-D-ribityl-3,4-xylidine with a novel chemical intermediate, 6-chloro-5-formyluracil.

12 Claims, No Drawings

SYNTHESIS OF 5-DEAZARIBOFLAVINE

BACKGROUND OF THE INVENTION

1. Field of the Invention

This invention relates to the synthesis of 5-deazariboflavine having the formula:

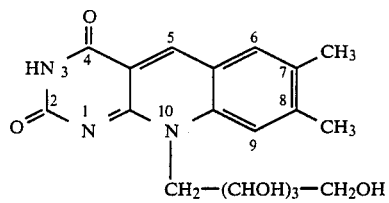

by condensing N-D-ribityl-3,4-xylidine with a novel chemical intermediate, 6-chloro-5-formyluracil.

2. Description of the Prior Art

Previously known processes for synthesizing 5-deazariboflavine include the following:

(1) A process of condensing 4,5-dimethyl-N-D-ribityl-anthranilaldehyde and barbituric acid. [Chem. Ind. (London), 204, 4–5 (1967), J. Heterocycl. Chem., 7(1), 99–105 (1970)];

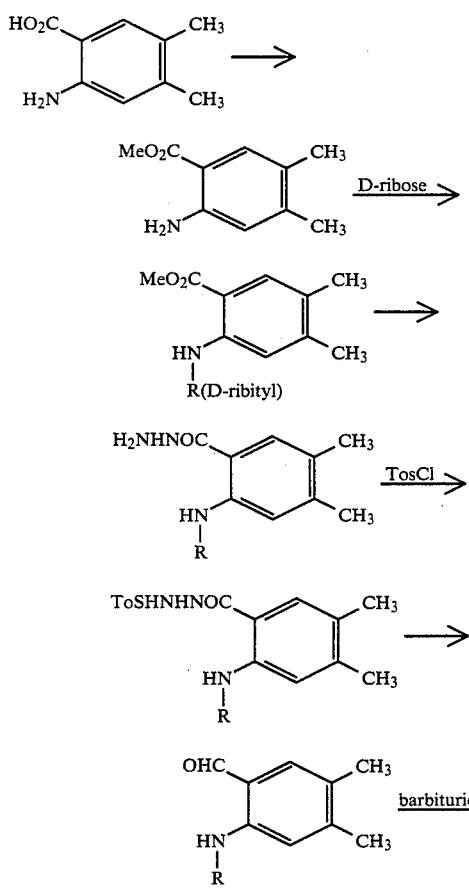

(2) A process of condensing 6-chlorouracil and N-D-ribityl-3,4-xylidine to obtain 6-(N-D-ribityl-3,4-xylidino)-uracil, which is acetylated with acetic anhydride in the presence of pyridine to obtain 6-[N-(tetra-O-acetyl-D-ribityl)-3,4-xylidino]-uracil, cyclizing by $POCl_3$ in dimethylformamide under heating, and deacetylating the thus obtained tetra-O-acetyl-5-deazariboflavine by methanolic ammonia, [Angew. Chem., 88(14), 475–476 (1976), Methods in Enzymology, Vol. 66, p. 267–276 (1980)];

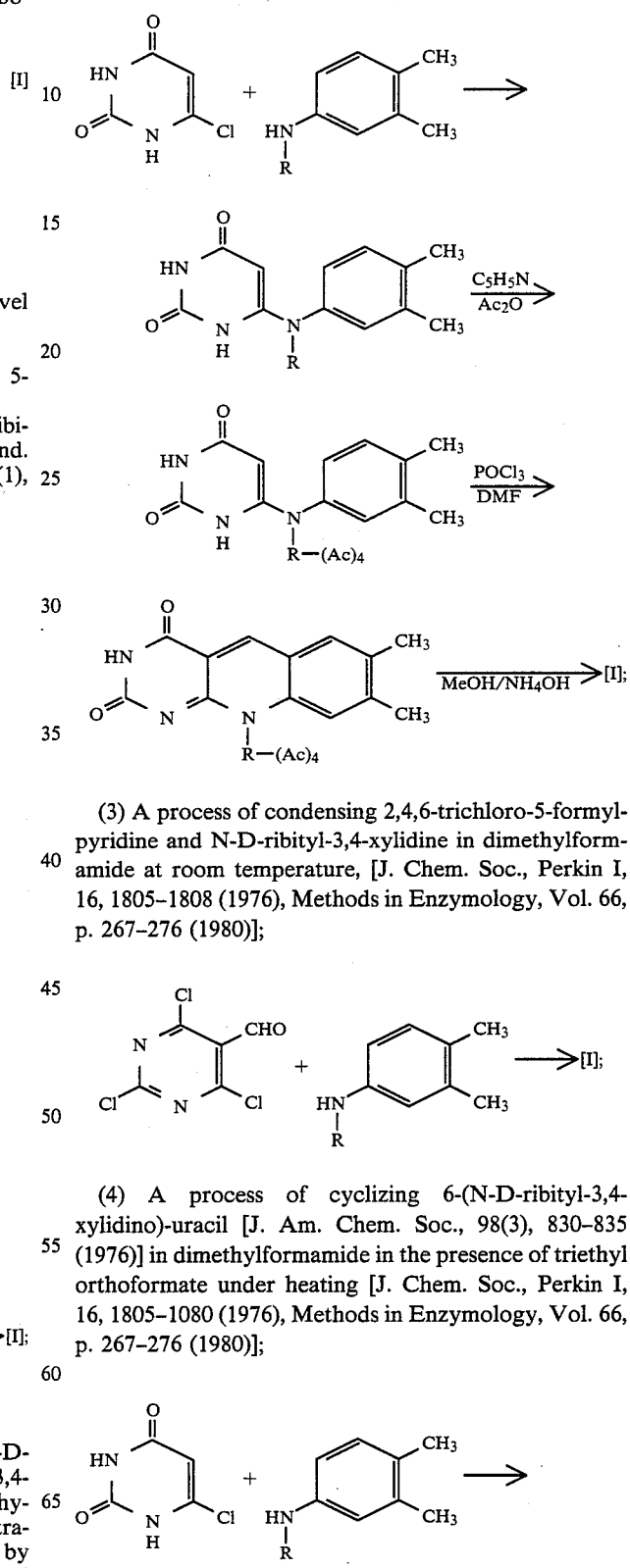

(3) A process of condensing 2,4,6-trichloro-5-formylpyridine and N-D-ribityl-3,4-xylidine in dimethylformamide at room temperature, [J. Chem. Soc., Perkin I, 16, 1805–1808 (1976), Methods in Enzymology, Vol. 66, p. 267–276 (1980)];

(4) A process of cyclizing 6-(N-D-ribityl-3,4-xylidino)-uracil [J. Am. Chem. Soc., 98(3), 830–835 (1976)] in dimethylformamide in the presence of triethyl orthoformate under heating [J. Chem. Soc., Perkin I, 16, 1805–1080 (1976), Methods in Enzymology, Vol. 66, p. 267–276 (1980)];

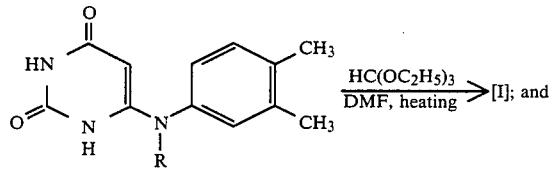

(5) A process of condensing 6-chlorouracil and N-D-ribityl-3,4-xylidine in water under heating to obtain 6-(N-D-ribityl-3,4-xylidino)-uracil, then cyclizing in the presence of trimethyl orthoformate and p-toluenesulfonic acid to obtain 2′,3′4′5′-bis-O-methoxymethylene-5-deazariboflavine, and heating the thus obtained product with hydrochloric acid [J. Heterocycl. Chem., 15(3), 489–491 (1978), U.S. Pat. No. 4,277,603 (July 7, 1981)].

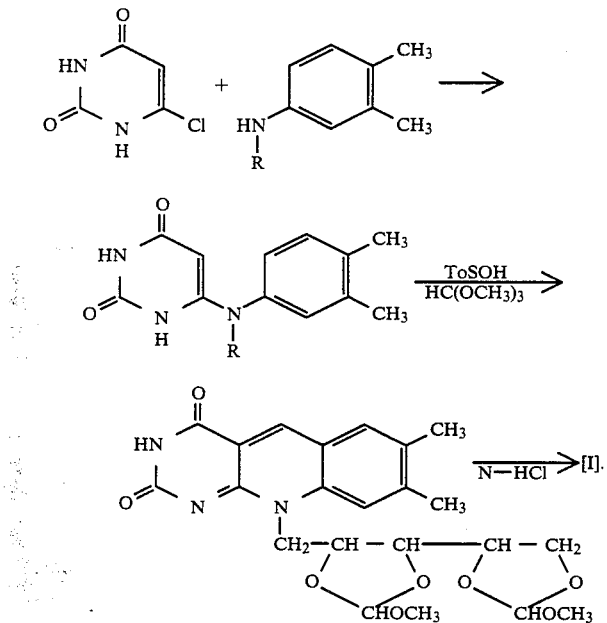

These preceding processes have a number of disadvantages.

Process (1) has many process steps and complex operations with low yield, and hence it is not an economical process.

Process (2) has many process steps, and a long synthesis, with a poor yield.

Although process (3) is a simple operable synthesis, the yield is quite low (37%) and therefore it is not industrially economical.

Process (4) is a two step synthesis, however its yield is quite low (44%) and therefore it also is not industrially economical.

Process (5) has a slightly shorter reaction process, however, its yield is low (25%) and therefore it also is not industrially economical.

5-deazariboflavine has been disclosed as a useful remedy for coccidiosis in Japanese published patent application No. 53-56698.

In the extensive discussion of Riboflavine in "The Merck Index", ninth edition, published by Merck & Co., Inc., Rahway, N.J., U.S.A. (1976) under monograph number 7993, it is stated that: "Riboflavin for therapeutic use is produced by synthesis, the most common starting materials being O-xylene, D-ribose, and alloxan". Various U.S. patents and published monographs are disclosed in monograph 7993, all of which are incorporated herein by reference. Of course riboflavine differs from the 5-deazariboflavine of this invention in that riboflavine has a nitrogen at the 5 position whereas the compound of this invention has a hydrogen (see above formula I).

SUMMARY OF THE INVENTION

In accordance with this invention, 5-deazariboflavine can be obtained by condensing 6-chloro-5-formuluracil and N-D-ribityl-3,4-xylidine in a one step reaction process.

The reaction process of the present invention is illustrated as follows:

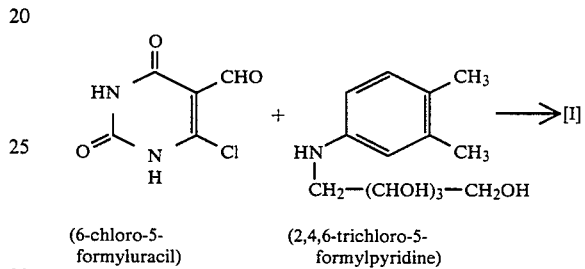

(6-chloro-5-formyluracil)        (2,4,6-trichloro-5-formylpyridine)

6-chloro-5-formyluracil of the above process is a novel compound, and can be synthesized by reacting 2,4,6-trichloro-5-formylpyridine [J. Chem. Soc., Perkin I, 16, 1805–1808 (1976)] with alkaline carbonate in an aqueous alcohol.

N-D-ribityl-3,4-xylidine is a known compound and its synthesis was reported in Angew. Chem., 88(14), 475–476 (1976).

DESCRIPTION OF THE PREFERRED EMBODIMENTS

The synthesis method of the present invention has the advantages of being simple and a high yield. It is therefore particularly useful for industrial production.

The condensation reaction of the above 6-chloro-5-formyluracil with N-D-ribityl-3,4-xylidine is carried out in an organic solvent under heating. Any commonly known organic solvent may be used, although dimethylformamide is preferred. The reaction temperature is at or below the boiling point of the organic solvent, in the case of dimethylformamide at or below about 153° C. The reaction time may vary depending upon other reaction heating conditions. The reaction can be stopped upon confirming the disappearance of D-ribityl-3,4-xylidine in the reaction mixture by silica-gel thin layer chromatography, liquid chromatography or high performance liquid chromatography.

Isolation and purification of 5-deazariboflavine from the reaction mixture can be accomplished by cooling the reaction mixture, filtering the precipitated crystals and recrystallizing from water after drying.

The chemical intermediate 6-chloro-5-formyluracil having the formula:

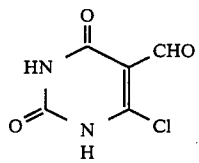

[II]

is itself a novel compound which forms one aspect of this invention. It may be synthesized in the following manner.

EXAMPLE 1

Synthesis of 6-chloro-5-formyluracil 2,4,6-trichloro-5-formylpyridine (8 g, 0.0378 mole) was added to a solution of potassium carbonate (5 g) dissolved in a mixture (300 ml) of ethanol and water (2:1), and stirred at room temperature for 3 hours. The reaction mixture was neutralized with acetic acid and the insolubles were filtered off, and the filtrate was allowed to stand in a freezing room overnight. Precipitated crystals were collected by filtration and dried to obtain a pale yellowish powder which was 6-chloro-5-formyluracil.

Yield: 5.94 g (90%).
m.p.: 165° C. (decomp.).
Mass (m/e): 174 (M+).

The product was unstable for recrystallization and was used as a chemical intermediate in a further reaction without purification.

EXAMPLE 2

Synthesis of 5-deazariboflavine 6-chloro-5-formyluracil (0.89 g, 5.1 m moles) and N-D-ribityl-3,4-xylidine (1.0 g, 3.9 m moles) were added to dimethylformamide (30 ml) and stirred at 100° C. for 4-5 hours. The reaction mixture was cooled, precipitated crystals were collected by filtration, dried and recrystallized from water to obtain pale yellowish crystals of 5-deazariboflavine.

Yield: 1.3 g (88.4%).
m.p.: 291° C.
Elementary analysis [$C_{18}H_{21}N_3O_6$]:

|  | C % | H % | N % |
| --- | --- | --- | --- |
| Calculated: | 57.47 | 5.64 | 11.20 |
| Found: | 57.47 | 5.65 | 11.16. |

General Synthesis Parameters

Where they are not already given above, the parameters of the two synthesis of this invention are as follows. Any parameters not otherwise specified may be considered as conventional and their choice would be apparent to someone of ordinary skill in this art, given the hindsight of the other portions of the disclosed invention.

Synthesis of 5-deazariboflavine

The mole ratios of the reactants 6-chloro-5-formyluracil and N-D-ribityl-3,4-xylidine are theoretically 1:1. However, it is preferred to use a slight excess such as a range of 1.0-1.4 moles, especially 1.1-1.4 moles, of 6-chloro-5-formyluracil per 1.0 mole of N-D-ribityl-3,4-xylidine. A mole ratio of about 1.3:1.0 is particularly preferred. The condensation is preferably conducted at atmospheric pressure and at a minimum temperature of 60° C. and a maximum temperature of the boiling point of the organic solvent. The preferred temperature range when commonly used organic solvents are employed is 60°-120° C.

Synthesis of 6-chloro-5-formyluracil

This compound is synthesized by reacting 2,4,6-trichloro-5-formylpyrimidine with an alkaline carbonate in an aqueous alcohol, preferably at atmospheric pressure and room temperature. A preferred alkaline carbonate is potassium carbonate. Since this is not a condensation reaction, the moles of 6-chloro-5-formyluracil produced are equivalent to the moles of 2,4,6-trichloro-5-formylpyrimidine starting material.

I claim:

1. A process for synthesizing 5-deazariboflavine comprising condensing 6-chloro 5-formyluracil with N-D-ribityl-3,4-xylidine in one step reaction in an organic solvent at a temperature at or below the boiling point of said solvent yielding greater than 80% of said 5-deazariboflavine.

2. The process of claim 1 wherein the temperature is minimum of 60 C.

3. The process of claim 2 wherein the organic solvent is dimethylformamide.

4. The process of claim 2 wherein the maximum temperature is 120° C.

5. The process of claim 1 wherein the condensation reaction is conducted at atmospheric pressure.

6. The process of claim 1 wherein the mole ratio is 1.0 mole of N-D-ribityl-3,4-xylidine to a slight excess over 1.0 mole of 6-chloro-5-formyluracil.

7. The process of claim 6 wherein the mole ratio is 1.0:1.0-1.4.

8. The process of claim 7 wherein the mole ratio is 1.0:1.1-1.4.

9. The process of claim 8 wherein the mole ratio is about 1.0:1.3.

10. The process of claim 1 wherein the mole ratio of N-D-ribityl-3,4-xylidine to 6-chloro-5-formyluracil is 1.0:1.0-1.4.

11. The process of claim 10 wherein the mole ratio is about 1.0:1.3.

12. The process of claim 1 wherein the condensation is continued until the N-D-ribityl-3,4-xylidine is consumed.

* * * * *